(12) United States Patent
Liu et al.

(10) Patent No.: US 9,056,208 B2
(45) Date of Patent: Jun. 16, 2015

(54) PERSONAL CARE COMPOSITIONS THAT INCLUDE ENROBED SUGAR

(71) Applicant: Conopco Inc., Englewood Cliffs, NJ (US)

(72) Inventors: Hongjie Liu, Trumbull, CT (US); Lin Yang, Trumbull, CT (US); Georgia Shafer, Trumball, CT (US)

( * ) Notice: Subject to any disclaimer, the term of this patent is extended or adjusted under 35 U.S.C. 154(b) by 138 days.

(21) Appl. No.: 13/761,993

(22) Filed: Feb. 7, 2013

(65) Prior Publication Data
US 2014/0220087 A1      Aug. 7, 2014

(51) Int. Cl.
| | |
|---|---|
| A61K 8/60 | (2006.01) |
| A61Q 19/10 | (2006.01) |
| A61Q 5/02 | (2006.01) |
| A61Q 19/00 | (2006.01) |
| A61K 8/31 | (2006.01) |
| A61K 8/02 | (2006.01) |

(52) U.S. Cl.
CPC ............ A61Q 5/02 (2013.01); A61Q 19/00 (2013.01); A61Q 19/10 (2013.01); A61K 8/60 (2013.01); A61K 8/31 (2013.01); A61K 8/0241 (2013.01); *A61K 2800/412* (2013.01); *A61K 2800/622* (2013.01); *A61K 2800/652* (2013.01)

(58) Field of Classification Search
None
See application file for complete search history.

(56) References Cited

U.S. PATENT DOCUMENTS

| | | | |
|---|---|---|---|
| 6,197,757 B1 * | 3/2001 | Perrier et al. | .................. 514/53 |
| 6,395,691 B1 | 5/2002 | Tsaur | |
| 6,730,651 B2 | 5/2004 | Hsu | |
| 6,932,982 B2 | 8/2005 | McIver | |
| 7,585,538 B2 | 9/2009 | Mangos | |
| 2002/0034479 A1 | 3/2002 | Green | |
| 2005/0100570 A1 | 5/2005 | Wei et al. | |

FOREIGN PATENT DOCUMENTS

| | | |
|---|---|---|
| EP | 0401956 A2 | 12/1990 |
| JP | 02262817 | 10/1990 |
| JP | 09208441 | 8/1997 |
| JP | 2001-238611 | 9/2001 |
| KR | 20070077017 | 7/2007 |
| KR | 20070077017 A | 7/2007 |
| KR | 2008009896 | 1/2008 |
| WO | WO2006088673 | 8/2006 |

OTHER PUBLICATIONS

Search Report in PCTEP2014051595, May 8, 2014.
Written Opinion in PCTEP2014051595, May 8, 2014.

* cited by examiner

*Primary Examiner* — Ernst V Arnold
(74) *Attorney, Agent, or Firm* — Ronald A. Koatz

(57) ABSTRACT

A personal care composition that comprises:
 a) a sugar infused with at least one additive, in particular, hair and/or skin benefit agent, wherein the infused sugar is coated with a hydrocarbon layer of selected viscosity and melting point;
 b) at least 10 wt % water, based on the total weight of the composition,
wherein the infused and coated sugar is suspended in the composition as a disperse particle phase.

16 Claims, No Drawings

PERSONAL CARE COMPOSITIONS THAT INCLUDE ENROBED SUGAR

FIELD OF THE INVENTION

This invention relates to personal care compositions for use on the human body that include enrobed sugar, the enrobed sugar preferably being a vehicle for delivery of one or more additives, including, but not limited to, skin and/or hair benefit agents.

BACKGROUND OF THE INVENTION

Skin and/or hair benefit agents, for example, anti-aging agents, skin optical agents, sun care agents and fragrance, to name a few, are among the ingredients commonly available in personal care compositions formulated as water based compositions. In many applications it is desirable that such ingredients be stably retained in such compositions during processing and storage, but that they become quickly available in use, that is to say, upon or after application. A common method of providing such rapid availability is to encapsulate the ingredients of interest in a delivery vehicle designed to release in response to a trigger associated with the intended use of the composition.

Their ability to be infused with a variety of different materials coupled with their relatively rapid solubility in water, makes sugars potentially attractive candidates as encapsulating vehicles for additives, in particular, skin and/or hair benefit agents, in a variety of personal care compositions, including, for example, cleansing products such as, for example, body washes, moisturizers, liquid soaps, shower gels, face washes, hand washes, shampoos, hair conditioners, body lotions, and the like. However, as many personal care compositions are water based, and sugars are highly water soluble, finding a means of stabilizing the sugars in such compositions without undesirably impacting their release properties, particularly in applications where rapid release is desired, has been problematic.

JP 2062817 discloses make-up compositions therein said to have a skin-moisturizing effect and to give excellent feeling to the skin, which compositions contain one or more types of wax capsules containing one or more skin-moisturizing components, for example, components selected from water, alcohols, polyhydric alcohols, sugars or sugar alcohols, sugar derivatives, polysaccharides, amino acids, polypeptides, organic acid salts, water-soluble vitamins and substances having vitamin-like action. Exemplary of the wax component of the capsule are beeswax or spermaceti, vegetable solid wax such as carnauba wax, mineral solid wax such as montan wax or Japan wax, and the like.

EP 0401956 discloses a sweetener delivery system therein said to be useful in chewing gum confectionary, comestibles, personal products and pharmaceutical compositions. The delivery system therein disclosed comprises a particulate sweetener encapsulated in a matrix consisting essentially of a blend of a fat and a rosin ester, such delivery system having a melting point of from about 60° C. to about 90° C.

U.S. Pat. No. 6,932,982 discloses a granular delivery system based on a matrix that combines a carbohydrate material with from 1 to 7 percent of prehydrated agar. The granular delivery system is therein said to be capable of providing controlled release of an active flavoring or perfuming ingredient that is encapsulated therein. In the field of perfuming ingredients, disclosed applications for the delivery system include detergents, fabric softeners, soaps, bath or shower gels, deodorants, body lotions, shampoos or other hair-care products, household cleansers, and cleaning and deodorizing blocks for toilet tanks.

US 2002/0034479 discloses oral compositions comprising petroleum jelly in the form of droplets enrobing a particulate active, characterized in that the droplets comprise an amphiphilic organic material capable of forming, upon contact with moisture, a water-insoluble liquid crystal phase of at least one dimensional periodicity. The amphiphilic organic material is therein defined as an organic material which has both hydrophobic and hydrophilic portions in its structure. At paragraph 0022, typical examples of amphiphilic organic materials are said to be "unsaturated and/or saturated $C_{12}$-$C_{24}$ fatty acid glycerides, optionally in admixture with long chain fatty acids and/or fatty alcohol and/or polyalkylene glycols such as glyceryl monooleate, optionally in admixture with oleic acid, glycerol monolaurate, in admixture with oleic acid or with oleyl alcohol, stearyl alcohol, isostearyl alcohol or a mixture thereof; glyceryl mono-isostearate, glyceryl monolinoleate in admixture with glyceryl mono-oleate, polyoxyethylene ethers, mixtures of lecithin and oleic acid or oleyl alcohol, mixtures of sodium or potassium oleate with oleic acid or oleyl alcohol, and certain silicone materials such as sodium 10-Ω-butyl [poly(dimethylsiloxy)dimethyl silyl]decanoate." The patent discloses that mixtures of any of these materials may also be used.

U.S. Pat. No. 6,730,651 discloses a stock composition for use in detergent or personal care compositions, the stock comprising a high concentration of capsules formed of a hydrophobic material such as, for example, paraffin, oil, wax or petroleum jelly.

KR 2008009896 discloses a cosmetic composition having a skin scrub function and a skin moisturizing function that includes recrystallized sugar particles.

U.S. Pat. No. 6,395,691 discloses a personal liquid composition comprising: (a) a surfactant system, (b) a particle-in-oil dispersion comprising: (i) petrolatum or thickened emollient oil which contains oil mixable polymers which petrolatum or thickened oil have a viscosity as therein more particularly described and (ii) particles selected from solids having a particle size of 0.1 to 250 microns and capsules in the size range of 1 to 200 microns, all as therein more particularly described. Examples of suitable particles are silica, talc, mica, silicone powders or capsules such as perfume capsules or vitamin E capsules.

In the area of personal care compositions for application to the human body, as for example, in the treatment of hair and/or skin, there remains a need for encapsulates that afford a combination of stability, particularly in aqueous products, and desirable release.

SUMMARY OF THE INVENTION

The present invention relates to a personal care composition that comprises,
  a) a sugar infused with at least one additive, the additive preferably comprising fragrance and/or skin and/or hair benefit agent, wherein the infused sugar is coated with a hydrocarbon layer having a melting point of from 30° C. to 70° C. and a viscosity of from 1 Pa·s to 200 Pa·s, preferably from 5 Pa·s to 50 Pa·s;
  b) at least 10 wt % water, based on the total weight of the composition,
  wherein the coated, infused sugar is suspended in the composition as a disperse particle phase.

DETAILED DESCRIPTION OF THE INVENTION

It has been found that by coating or enrobing sugar with a hydrocarbon having a particular melting point and viscosity, the sugar can be made sufficiently stable that it doesn't dissolve when suspended in a water-containing composition, yet is sufficiently sensitive to rupture by rubbing or the application of a relatively mild shear force, as for example, when the composition is applied, that it provides rapid release of the additive with which the sugar is infused.

The sugars employed herein generally include one or more water-soluble, crystalline materials known as carbohydrate mono- and disaccharides. Preferably the monosaccharides are selected from pentose and/or hexose sugars, with hexose sugars being of interest in one or more embodiments. In one or more preferred embodiments the monosaccharides are aldose sugars. Disaccharides of particular interest are derived from two monosaccharides, which monosaccharides are preferably hexose sugars. Disaccharides in which one or both of the monosaccharide units are derived from glucose are preferred in one or more embodiments. To aid in release, the sugars preferably have a solubility in water (at 25° C.) of at least 1 g/ml, preferably at least 1.5 g/ml and most preferably at least 2 g/ml.

Non-limiting examples of the sugars that may be employed herein are sucrose, glucose, fructose, and the like, and mixtures thereof, with sucrose being of particular interest. In one or more embodiments the coated (i.e., enrobed) sugars are "substantially free" of cyclodextrin and starch that is to say, if present, the total amount thereof is less than 1% by weight, based on the total weight of the coated sugar, with coated sugar that is entirely free of cyclodextrin and starch also being contemplated. In one or more embodiments the coated sugars are substantially free of carbohydrate polysaccharide, i.e., the total amount thereof is less than 0.5% by weight, based on the total weight of the coated sugar. As used herein the term "polysaccharide" is understood to exclude disaccharide.

The compositions in which the coated sugars are employed, may however, include starch, and/or other carbohydrate polysaccharides as thickening agents and/or viscosity modifiers. Moreover, encapsulates, i.e., encaps, based on cyclodextrin, starch and/or other polysaccharides may be optionally present in addition to the coated sugars. In one or more embodiments the total amount of carbohydrate polysaccharide is from 0 to 10% by weight, more particularly, less than 3% by weight, and even more particularly less than 1% by weight, based on the total weight of the composition. Also contemplated for use in the subject compositions are carbohydrate derived surfactants such as, for example, alkylpolyglycosides and polysaccharide amides.

The sugar may be infused with any of a variety of additives, e.g., colorant, fragrance, emotive and skin and/or hair benefit agent, typically at a total additive loading of from 0.1 to 50 wt more particularly from 1 to 30 wt %, and even more particularly from 5 to 30 wt %, based on the combined weight of additive and sugar. The additive may be water-soluble, as for example, in the case of humectants (glycerin, for example), nutritional supplements (e.g., vitamin C, vitamin $B_6$, and niacinamide), and botanical extracts (e.g. aloe vera) to name a few, or it may be water-insoluble, as for example in the case of typical fragrance oils. Materials contemplated for use as benefit agents are, for example, fragrance, pigment, moisturizer, sensory modifiers, anti-aging or anti-inflammatory agents, anti-oxidants, and the like. Desirably, the infused additives are compatible with the hydrocarbon layer or do not otherwise interfere with the application or retention thereof. In one or more embodiments of particular interest, the sugar is infused with fragrance and/or one or more skin and/or hair benefit agents.

The sugars can be infused with additive by various means, the choice of which is not particularly limited and largely depends, on the properties of the additive being so infused. For example, it may be possible to spray coat the additive onto the sugar; such a coating means is of interest when the additive is a normally liquid material, or is solubilized in a normally liquid material that does not solubilize the sugar. Alternatively, the sugar may be crystallized out of a solution that contains the additive. Methods of sugar infusion are disclosed, for example, in N. J. Zuidam (Encapsulation Technologies for Active Food Ingredients and Food Processing), Jamileh M. Lakkis (Encapsulation and controlled release technologies in food systems, 2007), Reineccius, 2004 (Reineccius, G. A., Spray-drying of food flavours, Drying Technology 22(6), 1289-1324, 2004) & Porzio, 2004 (Porzio, M., Flavor encapsulation: a convergence of science and art, Food Technology, 58(7), 40-47, 2004), incorporated herein by reference.

The hydrocarbon layer that serves as a coating for the infused sugar typically has a melting point of from 30° C. to 70° C., more particularly from 30° C. to 60° C., even more particularly from 35° C. to 50° C. The hydrocarbon layer, i.e., the composition constituting the hydrocarbon layer, has a viscosity of from 1 Pa·s to 200 Pa·s, preferably from 1 Pa·s to 100 Pa·s, even more preferably from 5 Pa·s to 50 Pa·s. Viscosity is conveniently measured by a AR-G2 rheometer from TA Instruments (or equivalent), at shear rate of $10\ s^{-1}$ and temperature of 25° C., using standard 40 mm steel parallel plates with gap of 200 um. melting point and viscosity parameters of the hydrocarbon layer generally describe material that is gel-like or semi-solid under normal conditions and may alternatively be referred to as "structured oil". The structured oil aids in stably suspending the sugar in the compositions of interest.

The hydrocarbon layer may comprise oil having a viscosity as described above. It is also possible that the viscosity of the hydrocarbon layer is achieved by thickening a lower viscosity oil with one or more oil-miscible thickening agents. Preferably the hydrocarbon layer comprises one or semi-solids identified by CAS number 8009-03-8, (known by the common names petrolatum, petroleum jelly, and soft paraffin) and/or emollient oil structured/thickened with oil mixable polymers. Examples of suitable emollient oils are mineral oils, triglyceride oils such as sunflower seed oil, castor oil or soybean oil, alkyl esters such as isopropyl palmitate or isopropyl myristate and silicone oils. To achieve desirable viscosities, such emollient oils may be required to be thickened with, for example, an oil-miscible thickening agent such as, for example, hydrogenated or non-hydrogenated polymer of alkylene or isoalkylene such as polybutene, poly-alphaolefin, or polyester, polyacrylate polymers and copolymers, and rubber thermoplastic block copolymers such as butadieneistyrene or styrene/butylene di- or tri-block copolymers. Included among the preferred oil mixable polymers are rubber based thermoplastic block copolymers available from Shell Chemical Company under the tradename of Kraton®.

In one or more preferred embodiments the hydrocarbon layer comprises petrolatum.

In addition to the hydrophobic layer helping to keep the coated sugar stably suspended, the size and density of the coated sugar are additional factors that impact composition stability. Larger, denser particles are, in general, more susceptible to settling than smaller, less dense particles. In general, the average primary particle size of the coated, infused sugar is in from 50 μm to 3000 μm, more particularly from 100 μm to 2000 μm, even more particularly from 500 μm to 1500 μm. Clustering may give rise to particle aggregates outside of such ranges, particularly when mixed with hydrocarbon oils. Cluster formation may be minimized through the control of processing conditions such as, for example, choice of equipment, temperature, mixing speed, and the like. In one or more embodiments, at least 75 wt %, more particularly at least 50 wt % of the coated, infused sugar has a particle size in the range of from 500 um to 1500 um.

The sugar density, prior to infusion and coating, typically varies from 0.5 gram/cm$^3$ to 1.6 gram/cm$^3$, due to differences in particle size, shape and inclusion of moisture. For many compositions, coated sugar having a density of from 0.5 g/cm$^3$ to 1.2 g/cm$^3$, preferably from 0.8 g/cm$^3$ to 1.2 g/cm$^3$, is of particular interest. To minimize settling or separation, it is often preferable that the density of the coated sugar approximates that of the overall composition. Having a sufficiently high ratio of hydrocarbon layer to the uncoated, infused sugar can help to lighten the sugar particles. A weight ratio of hydrocarbon layer to the infused uncoated sugar of from 0.5 to 20, more particularly from 0.5 to 10, even more particularly from 1 to 5 is of interest in one or more embodiments. The ratios of preference depend in part on the desired tactile and sensory properties, product appearance and manufacturing conditions.

In addition to particle size and density, composition viscosity can also play a role in stabilizing the dispersed particles. Composition viscosity is determined, in part, by the end use compositions of interest. In one or more embodiments the composition desirably has a viscosity in a range of from 0.1 Pa·s to 100 Pa·s, more particularly from 1 Pa·s to 20 Pa·s. Viscosity is conveniently measured by a AR-G2 rheometer, TA Instruments (or equivalent), at shear rate of 10 s$^{-1}$ and 25° C., using standard 40 mm steel parallel plates with gap of 200 um.

The coated, infused sugar should preferably remain stably suspended in the subject compositions at 25° C. for at least 3 months without visible physical separation, i.e., without separation visible to the naked eye without the aid of instrumentation or visual enhancement.

The coating sugar may be formed by any of a variety of techniques including spin coating, co-extrusion, grinding, or simple mixing. Preferably coating of the sugar is carried out at temperature 5-10° C. higher than the melting point of the coating material.

In one or more embodiments, the coated sugar may be formulated as a dispersion of infused sugar in the material comprising the hydrocarbon layer. In such instances the material comprising the hydrocarbon layer typically comprises 30 wt. % to 95 wt. %, preferably 50 wt. % to 80 wt. % of the dispersion; conversely, the infused sugar comprises 5 wt. % to 70 wt. %, preferably 20 wt % to 50 wt % of the dispersion.

The amount of coated sugar depends, in part, on the additive infused therein, the amount of additive relative to the coated sugar, and the intended use of the composition. In many applications the coated sugar is present in an amount of 1% to 30 wt %, more particularly from 1% to 10 wt %, based the total weight of the composition.

As noted above, water is present in an amount of at least 10 wt %, based on the total weight of the composition. In one or more embodiments of interest, water is present in an amount of 30% to 90 wt %, more particularly 50% to 80 wt %, based on the total weight of the composition.

The compositions may be formulated into a variety of personal care products including, in particular, compositions in the form of structured liquids for topical application to the skin and/or hair such as, for example, body washes, moisturizers, liquid soaps, shower gels, face washes, hand washes, shampoos, hair conditioners, body lotions, and the like. The compositions referred to as "structured liquids" are liquids or gels that that include surfactant or other structuring systems, e.g., rheology modifiers, thickening agents, and the like. A micellar structure, e.g., be it a lamellar, spherical, cylindrical or other micellar structure, is typical of many structured liquids.

Cleansing compositions, including for example, body washes and shampoos, are of particular interest in one or more embodiments. The cleansing compositions are commonly in the form of micellar liquids, in particular, liquids that include micellar structures dispersed in an aqueous or other polar phase. In cleansing compositions the micellar structures, also known as micelles, are typically aggregates of surfactant molecules. Aggregation of surfactant typically results in a structure in which the polar or hydrophilic head of the surfactant molecules forms an outer region that surrounds a core formed from the non-polar or hydopobic tail region of the surfactant molecules. While often elongated, rod shaped, worm-like, or spherical in appearance, micelle geometry is subject to variation and is determined, in part, by choice and level of surfactant. The cleansing compositions may also take the form of micro-emulsions, i.e., optically isotropic and thermodynamically stable dispersions of immiscible liquids stabilized by surfactant, in which the dispersed phase commonly has a droplet size of less than 100 nm.

Cleansing compositions are characterized by the presence of one or more cleansing or detersive surfactants, which are typically present in a total amount of from 5 to 30 wt %, based on the total weight of the composition. The cleansing surfactants in the composition may be anionic, nonionic, amphoteric/zwitterionic, cationic or mixtures thereof.

The anionic surfactant may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGES); or an aromatic sulfonate such as alkyl benzene sulfonate. The anionic surfactant may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having about 8 to about 22 carbons, preferably about 8 to about 18 carbons, more preferably about 12 to about 18 carbons; n has an average value of greater than 1.0, preferably between 2 and 3; and M is a solubilizing cation such as, for example, sodium potassium, ammonium or substituted ammonium. Ammonium and sodium laurel ether sulfates are preferred.

The anionic surfactant may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, and acyl isethionates.

Sulfosuccinates tray be monoalkyl sulfosuccinates having the formula:

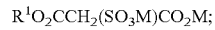
$$R^1O_2CCH_2(SO_3M)CO_2M;$$

and amido-MEA sulfosuccinates of the formula:

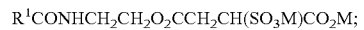
$$R^1CONHCH_2CH_2O_2CCH_2CH(SO_3M)CO_2M;$$

wherein in such formulas $R^1$ ranges from $C_6$-$C_{22}$ alkyl and M is a solubilizing cation as described above; or amido-MIPA sulfosuccinates of formula:

$$RCONH(CH_2)CH(CH_3)(SO_3M)CO_2M$$

wherein R and M are as described above.

Also included are the alkoxylated citrate sulfosuccinates; and alkoxylated sulfosuccinates such as the following:

R—O—(CH$_2$CH$_2$O)$_m$C(O)—CH$_2$CH(SO$_3$M)CO$_2$M)

wherein m=1 to 20; and R and M are as described above.

Sarcosinates are generally indicated by the formula R$^2$CON(CH$_3$)CH$_2$CO$_2$M, wherein R$^2$ ranges from C$_8$ to C$_{20}$ alkyl and M is a solubilizing cation.

Taurates are generally identified by formula:

R$^2$CONR$^3$CH$_2$CH$_2$SO$_3$M wherein R$^2$ is described above, R$^3$ ranges from C$_1$-C$_4$ alkyl and M is a solubilizing cation.

Another class of avionics are carboxylates such as follows:

R$^2$(CH$_2$CH$_2$O)$_p$M wherein R$^2$ is as described above, p is 0 to 20, and M is a solubilizing cation. Yet another carboxylate which can be used is amido alkyl polypeptide carboxylates such as, for example, is available from Seppic under the trademark Monteine®.

Another surfactant which may be used herein are the C$_8$-C$_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms. Acyl isethionates, when present, will generally range from 0.5-15% by weight, preferably from 1 to 10% by weight, based on the total weight of the cleansing composition. The acyl isethionate may be an alkoxylated isethionate such as is described in Ilardi et al., U.S. Pat. No. 5,393,466, incorporated herein by reference.

In general, the anionic component will comprise from 1 to 20% by weight, preferably from 2 to 15% by weight, most preferably from 5 to 12% by weight of the cleansing composition.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for many of these compounds is:

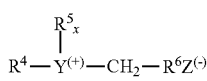

wherein R$^4$ contains an alkyl, alkenyl, or hydroxy alkyl radical of from about 8 to about 18 carbon atoms, from 0 to about 10 ethylene oxide moieties and from 0 to about 1 glyceryl moiety: Y is selected from the group consisting of nitrogen, sulfur and phosphorous atoms; R$^5$ is an alkyl or monohydroxyalkyl group of from about 1 to about 3 carbon atoms; x is 1 when Y is a sulfur atom, and 2 when Y is a nitrogen or phosphorus atom; R$^6$ is an alkylene or hydroxyalkylene of from about 1 to about 4 carbon atoms and Z is a radical selected from the group consisting of carboxylate, sulfonate, sulfate, phosphonate, and phosphate groups.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

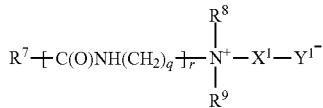

where R$^7$ is alkyl or alkenyl of 7 to 18 carbon atoms; R$^8$ and R$^9$ are each independently alkyl, hydroxyalkyl or carboxyalkyl of 1 to 3 carbon atoms; q is 2 to 4; r is 0 to 1; X$^1$ is alkylene of 1 to 3 carbon atoms optionally substituted with hydroxyl, and Y$^1$ is —CO$_2$— or —SO$_3$—.

Suitable amphoteric detergents within the above general formula include simple betaines of formula:

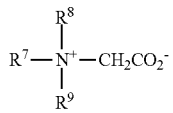

and amido betaines of formula:

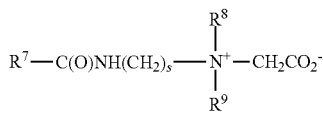

where s is 2 or 3. In both formulae R$^7$, R$^8$ and R$^9$ are as previously described R$^7$ may, in particular, be a mixture of C$_{12}$ and C$_{14}$ alkyl groups derived from coconut so that at least half, preferably at least three quarters of the groups R$^7$ have 10 to 14 carbon atoms. R$^8$ and R$^9$ are preferably methyl.

A further possibility is that the amphoteric detergent is a sulphobetaine of or a

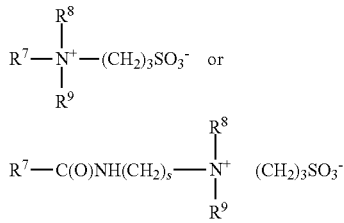

where s is as previously described, and preferably is 2, or variants of these in which —(CH$_2$)$_3$SO$_3$$^-$ is replaced by —CH$_2$C(OH)HCH$_2$SO$_3$$^-$. In these formulae R$^7$, R$^8$ and R$^9$ are as discussed previously. Amphoacetates and diamphoacetates are also intended to be covered in possible zwitterionic and/or amphoteric compounds which may be used.

The composition may optionally comprise a nonionic surfactant. The nonionic cleansing surfactant which may be used herein includes, in particular, the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl (C$_6$-C$_{22}$) phenols-ethylene oxide condensates, the condensation products of aliphatic (C$_8$-C$_{18}$)

primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic surfactant may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, incorporated herein by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also herein incorporated by reference.

Preferred alkyl polysaccharides are alkylpolyglycosides of the formula:

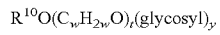

$$R^{10}O(C_wH_{2w}O)_t(glycosyl)_y$$

wherein $R^{10}$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; w is 0 to 3, preferably 2; t is from 0 to about 10, preferably 0; and y is from 1.3 to 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Nonionic surfactant generally comprises 0 to 10% by weight of the cleansing composition.

Cationic synthetic surfactant should not serve as the sole surfactant in the subject compositions, but can be optionally used as a co-surfactant at a lower level of from 0.5% to 6% by weight. The more preferred types of cationic surfactant are selected from the group consisting of: alkyl trimonnium chloride and methosulfate, and dialkyldimonnium chloride and methyl sulphate, and alkyl alkonium chloride and methyl sulphate and mixtures thereof. These surfactants contain 12 to 14 carbon atoms per alkyl chain. The most preferred cationic is selected from the group consisting of stearalkonium chloride, stearyltrimonium chloride, di-stearyl-dimonium chloride, and mixtures thereof.

The viscosity of the personal care composition may be modified by the inclusion of one or more thickening agents. Thickening agents suitable for use herein include, for example, organic, inorganic or polymeric stabilizer. Generally the organic polymeric stabilizer include, but are not limited to any of several long chain acyl derivatives or mixtures thereof. Included are the glycol mono- di- and triesters having about 14 to about 22 carbon atoms. Preferred glycol esters include the ethylene glycol mono- and distearates, glyceryl stearates, palm oil glyceride, tripalmitin, tristearin and mixtures thereof. Another example of suspending agent useful in the present invention include the alkanolamides having from about 14 to about 22 carbon atoms. Preferred alkanolamides are stearic monoethanolamide, stearic diethanolamide stearic monoisopropanolamide, stearic monoethanolamide stearate and mixtures thereof. Still another example of a suspending agent useful in the present invention include the long chain fatty acid esters such as stearyl stearate, stearyl palmitate, palmityl palmitate, trihydroxystearylglycerol and tristearylglycerol. Still another example of a suitable suspending agent useful in the present invention include the long chain amine oxides having from about 14 to about 22 carbon atoms. Preferred amine oxides are hexadecyldimethylamine oxide and octadecyldimethylamide oxide.

Examples of suitable polymeric suspending agent (or thickening agent) useful in the present invention include the carbohydrate gums such as cellulose gum, microcrystalline cellulose, cellulose gel, hydroxyethyl cellulose, hydroxypropyl cellulose, sodium carboxymethylcellulose, hydroxymethyl carboxymethyl cellulose, hydroxymethyl carboxypropyl cellulose, methyl cellulose, ethyl cellulose, guar gum, gum karaya, gum tragacanth, gum arabic, gum acacia, gum agar, xanthan gum and mixtures thereof. Preferred carbohydrate gums are the cellulose gums and xanthan gum. Of all the above described types of suspending agents, preferred compounds include the long chain glycol ester and the carbohydrate gums. Other stabilizers which may be used are set forth in U.S. Pat. No. 5,854,293 to Glenn. Jr. at column 4, line 36 to column 6, line 65, incorporated herein by reference.

The thickener may also be a cationic polymer. Suitable cationic polymers include Guar hydroxypropyltrimonium chloride, Quaternium-19, -23, -40, -57, poly(dimethyidiallylammonium chloride), poly(dimethyl butenyl ammonium chloride)-, w-bis(triethanolammonium chloride), poly(dipropyidiallylammonium chloride), poly(methyl-beta propaniodiallylammonium chloride), poly(diallylpiperidinium chloride), poly(vinyl pyridinium chloride), quaternised poly (vinyl alcohol), quaternized poly (dimethylaminoethylmethacrylate) and mixtures thereof.

Salt can also assist in building composition viscosity. In micellar liquids, salt helps promote micelle formation. Cosmetically acceptable organic or inorganic salts may be employed herein, so long as the salts are sufficiently soluble in the structured liquid and do not interact with other composition components to give insoluble species or undesirable complexes. Monovalent salts are generally less prone to form complexes and are preferred in one or more embodiments. Alkali metal salts, especially sodium and potassium salts are of particular interest, with alkali metal citrates and acetates, and chlorides being among the salts of particular interest, with sodium chloride and potassium chloride being preferred in one or more embodiments.

The thickening agent is typically present in an amount up to 10 wt %, more particularly, from 01 to 10 wt %, based on the total weight of the composition Other Ingredients In addition to ingredients noted above, the subject compositions may comprise any one of various ingredients which may be found in personal care compositions, including organic solvents (e.g., polyols such as $C_1$ to $C_4$ alkanols), auxiliary thickeners, sequestering agents (e.g., tetrasodium ethylenediaminetetraacetate), coloring agents, fragrance opacifiers, and pearlizers, pH adjusters, UV filters, and vitamins. The compositions may also include antimicrobial agents, alkanolamides, antioxidants (e.g., butylated hydroxytoluene), exfoliants (polyoxyethylene beads), etc.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above. In specifying any range of concentration or amount, any particular upper concentration or amount can be associated with any particular lower concentration or amount. Reported ranges are inclusive of their endpoints.

Except in the operating and comparative examples, or where otherwise explicitly indicated, all numbers in this description indicating amounts, parts percentages, ratios and proportions of material and conditions of reaction ought to be understood as modified by the word "about".

The following examples will more fully illustrate the embodiments of this invention. The Examples are not intended to limit the scope of the invention in any manner. All parts, percentages and proportions referred to herein and in the appended claims are by weight unless otherwise indicated.

EXAMPLE 1

Flavor infused sugar (sucrose) from IFF Inc. (i.e., Caplock™ Blueberry WONF or Caplock™ Pomegranate, such sugars being comparable in structure and granule size (0.2-2 mm)) were coated (enrobed) by different types of hydrophobic materials. The coating materials are further described in Table 1. Unless otherwise indicated, the reported viscosities were measured by the procedure described above ($10\ s^{-1}$ and 25° C.).

TABLE 1

Hydrophobic Coating Materials

| Coating materials | Viscosity (25° C.) | Melting point (° C.) |
|---|---|---|
| Mineral oil | 0.01 Pa·s | Liquid @ 25° C. |
| Petrolatum | 23.5 Pa·s | 30-35° C. |
| Polybutene 1 | 76 Pa·s[1] | Viscous Liquid @ 25° C. |
| Polybutene 2 | 517 Pa·s[1] | Viscous Liquid @25° C. |
| *Ricinus Communis* Seed Oil/Hydrogenated Castor Oil (obtained from Vertellus under the trademark Castorlatum ®) | 14,700 cP[1] | 71° C. |
| Shea Butter from ISP | Waxy solid | 31-36° C. |
| Partially Hydrogenated Soy (Iodine value ~70) | 20-30 Pa·s | 35-40° C. |

[1]As reported by the supplier.

The flavored sugar was coated (enrobed) with hydrophobic coating material in solid form by manual grinding with a porcelain pestle (16 cm long) and a mortar (13 cm diameter) at room temperature (25° C.). The hydrophobic coating material in liquid form and sugar were simply mixed by an overhead mixer at speed of 250 rpm.

Body wash formulations as described in Table 2 were prepared following conventional preparative techniques. The compositions were adjusted to the indicated pH as indicated by the addition of sodium hydroxide.

TABLE 2

Body Wash Base Formulations

| Ingredient (wt. %, as active) | Body Wash A | Body Wash B |
|---|---|---|
| Sodium Laureth Ether Sulfate -1EO (SLES) | 9.0 | 2.9 |
| Cocamidopropyl Betaine | 1.7 | 0 |
| Cocamide monoethanolamine (CMEA) | 1.3 | 0 |
| SLES/CMEA Preblend) (mass ratio 8:1) | 0 | 9.1 |
| Acrylates copolymer (Carbopol © Aqua SF-1; Lubrizol) | 2.4 | 2.0 |
| Tetrasodium EDTA | 0.05 | 0.05 |
| Preservative | 0.1 | 0.1 |
| Water | to 100 | to 100 |
| pH | 5.5-6.5 | 5.5-6.8 |

Using an extrusion or mixing procedure, the coated sugar was incorporated into the body wash formulations to prepare samples as described in Table 3. In the extrusion procedure, a plastic static mixer with defined orifice of 3 mm or a plastic syringe with catheter tip (60 ml) was used to extrude the enrobed sugar into the formulations at room temperature (25° C.). In the mixing procedure, the enrobed sugar sample was heated at 60° C. and poured into body wash A or B (as indicated) that was stirred by an overhead mixer at room temperature (25° C.) and 150 rpm. The process conditions were controlled to minimize clustering and to retain the structure integrity of the enrobed sugar. The stability of the coated sugar in the resulting samples was evaluated at the storage conditions reported in Table 3.

TABLE 3

Stability of Coated Sugar in Body Wash

| Sample | Coating Material | Coated Sugar Content of Body Wash (Wt. %) | Mass ratio (Coating Material/Sugar) | Storage temperature | Storage time | Preparation method | Body Wash Formulation | Stability of Coated Sugar In Body Wash |
|---|---|---|---|---|---|---|---|---|
| #1 | Mineral Oil | 10% | 1:1 | 50° C. | Overnight | Mixing | A | Dissolved |
| #2a | Polybutene 1 | 10% | 1:1 | 50° C. | Overnight | Mixing | A | Dissolved |
| #2b | Polybutene 1 | 5% | 1:1 | 50° C. | Overnight | Extrusion | A | Dissolved |
| #3 | Polybutene 2 | 5% | 1:1 | — | — | — | — | * |
| #4 | Petrolatum | 5% | 5:1 | 37° C. | 6 Weeks | Extrusion | A | Good—Sugar Integrity Retained |
| #5 | Petrolatum | 5% | 10:1 | 37° C. | 6 Weeks | Extrusion | A | Good—Sugar Integrity Retained |
| #6a | Petrolatum | 10% | 1:1 | 45° C. | 2 Weeks | Mixing | A | Dissolved |
| #6b | Petrolatum | 10% | 1:1 | 45° C. | 2 Weeks | Extrusion | A | Dissolved |
| #7 | Petrolatum | 10% | 1:1 | 25° C. | 3 Months | Extrusion | B | Good—Sugar Integrity Retained |
| #8 | Petrolatum | 10% | 1:1 | 37° C. | 2 Weeks | Extrusion | B | Good—Sugar Integrity Retained |
| #9 | Petrolatum | 10% | 1:1 | 25° C. | 1 hour | Mixing** | A | Dissolved |
| #10a | Castorlatum | 5% | 5:1 | 25° C. | Overnight | Mixing | A | Dissolved |
| #10b | Castorlatum | 5% | 5:1 | 25° C. | Overnight | Extrusion | A | Dissolved |

TABLE 3-continued

Stability of Coated Sugar in Body Wash

| Sample | Coating Material | Coated Sugar Content of Body Wash (Wt. %) | Mass ratio (Coating Material/Sugar) | Storage temperature | Storage time | Preparation method | Body Wash Formulation | Stability of Coated Sugar In Body Wash |
|---|---|---|---|---|---|---|---|---|
| #11a | Shea Butter | 5% | 5:1 | 25° C. | Overnight | Mixing | A | Dissolved |
| #11b | Shea Butter | 5% | 5:1 | 25° C. | Overnight | Extrusion | B | Dissolved |
| #12a | Partially Hydrogenated Soy | 5% | 5:1 | 25° C. | Overnight | Mixing | A | Dissolved |
| #12b | Partially Hydrogenated Soy | 5% | 5:1 | 25° C. | Overnight | Mixing | B | Dissolved |

\* Did not proceed; resulting composition was too viscous for a conventional body wash and not readily spread.
\*\*Stirred by overhead mixer at speed at 500 rpm for 10 minutes

EXAMPLE 2

A shampoo illustrative of the present invention is illustrated in the table below.

| Chemical Name | Wt. % (as active) |
|---|---|
| Sodium Laureth Sulfate | 17.14 |
| Cocamidopropyl Betaine | 5.333 |
| Guar Hydroxypropyltrimonium Chloride | 0.2 |
| Octamethylcyclotetrasiloxane | 1.67 |
| Glycol Distearate | 2.4 |
| Polyacrylate polymer (Carbopol ® 980; Lubrizol) | 0.4 |
| DMDM Hydantoin | 0.1 |
| Enrobed Sugar | 5-10 |
| Methylchloroisothiazolinone | 0.06 |
| Sodium Chloride | 0.8 |
| PPG-12 | 0.1 |
| Fragrance | 0.5 |
| Water | to 100 |
| pH | 5.5-6.5 |

EXAMPLE 3

A lotion illustrative of the present invention is illustrated in the table below.

| Ingredient Name | wt % (as active) |
|---|---|
| Glycerin | 10.0 |
| Titanium Dioxide | 0.1 |
| Magnesium Aluminum Silicate | 0.2 |
| Carbopol ® Ultrez 21 Acrylates/C10-30 Alkyl Acrylate Cross Polymer; Lubrizol | 0.2 |
| Potassium Hydroxide | 0.6 |
| Stearic Acid | 4.3 |
| Cetyl Alcohol | 0.5 |
| Glyceryl Stearate | 0.9 |
| Isopropyl Palmitate | 0.6 |
| Methylparaben | 0.2 |
| Panthenol | 0.1 |
| Dihydroxypropyltrimonium Chloride | 0.1 |
| Enrobed Sugar | 5-10 |
| Phenoxyethanol | 0.4 |
| Water | to 100 |

What is claimed is:

1. A personal care composition that comprises:
   a) a sugar infused with at least one additive, wherein the infused sugar is coated with a hydrocarbon layer having a melting point of from 30° C. to 60° C. and a viscosity of from 1 Pa·s to 200 Pa·s and
   b) at least 10 wt % water, based on the total weight of the composition,
   wherein the coated, infused sugar is suspended in the composition as a disperse particle phase
   wherein the sugar has a solubility in water, when measured at 25° C., of equal to or greater than 1 g/ml.

2. The composition according to claim 1 wherein the ratio, by weight, of hydrocarbon layer to uncoated, infused sugar is from 0.5 to 10.

3. The composition according to claim 1 wherein the hydrocarbon layer comprises petrolatum.

4. The composition according to claim 1 wherein the hydrocarbon layer comprises thickened emollient oil.

5. The composition according to claim 1 wherein the composition is in the form of a cleansing composition and further comprises at least one cleansing surfactant.

6. The composition according to claim 1 wherein the infused sugar is mono- and/or disaccharide.

7. The composition according to claim 1 wherein the infused sugar comprises sucrose.

8. The composition according to claim 3 wherein the petrolatum has a viscosity in the range of 5 Pa·s to 50 Pa·s.

9. The composition according to claim 5 wherein the cleansing surfactant comprises anionic surfactant.

10. The composition according to claim 1 wherein the sugar is infused with at least one fragrance additive.

11. The composition according to claim 1 wherein the coated, infused sugar is present in the composition in an amount of from 1 to 30 wt %, based on the total weight of the composition.

12. The composition according to claim 1 wherein water comprises from 1 to 80 wt % of the composition.

13. The composition according to claim 1 wherein the coated, infused sugar has an average particle size of from 50 um to 3000 um.

14. The composition according to claim 1 wherein the coated, infused sugar has a density of from 0.8 g/cm$^3$ to 1.2 g/cm$^3$.

15. The composition according to claim 1 wherein the sugar is infused with at least one skin and/or hair benefit agent.

16. The composition according to claim 1, wherein the composition is in the form of a structured liquid.

\* \* \* \* \*